US011245743B1

(12) United States Patent
Mitchell et al.

(10) Patent No.: US 11,245,743 B1
(45) Date of Patent: *Feb. 8, 2022

(54) BANDWIDTH DEPENDENT MEDIA STREAM COMPRESSION

(71) Applicant: Architecture Technology Corporation, Minneapolis, MN (US)

(72) Inventors: Tyler J. Mitchell, Ithaca, NY (US); Judson Powers, Ithaca, NY (US); Scott Aloisio, Willseyville, NY (US); Matthew A. Stillerman, Ithaca, NY (US); Valentino Felipe, Campbell, CA (US)

(73) Assignee: Architecture Technology Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,454

(22) Filed: Sep. 25, 2020

Related U.S. Application Data

(63) Continuation of application No. 16/015,116, filed on Jun. 21, 2018, now Pat. No. 10,812,562.

(51) Int. Cl.
  *G06F 15/16* (2006.01)
  *H04L 29/06* (2006.01)
  (Continued)

(52) U.S. Cl.
  CPC .............. *H04L 65/80* (2013.01); *G06T 7/194* (2017.01); *H04L 47/801* (2013.01);
  (Continued)

(58) Field of Classification Search
  CPC ... H04L 65/80; H04L 47/801; H04L 65/4084; H04L 65/601; G06T 7/194; G06T 2207/10021; G16H 40/67
  (Continued)

(56) References Cited

U.S. PATENT DOCUMENTS 5,764,306 A * 6/1998 Steffano ............... G11B 27/034
  348/552
5,821,997 A   10/1998 Kawamura et al.
  (Continued)

FOREIGN PATENT DOCUMENTS

JP   2011234288 A   11/2011

OTHER PUBLICATIONS

Amin Safaei, Q. M. Jonathan Wu, Yimin Yang, System-on-a-chip (SoC)-based hardware acceleration for foreground and background identification, Journal of the Franklin Institute, vol. 355, Issue 4, 2018, p. 1888-1912 (Year: 2018).*
  (Continued)

*Primary Examiner* — Taylor A Elfervig
(74) *Attorney, Agent, or Firm* — Shumaker & Sieffert, P.A.

(57) ABSTRACT

In general, this disclosure describes media stream transmission techniques for a computing device. The computing device may capture an image of a local background environment. The computing device may record a first media stream that includes at least a portion of the image of the background environment and at least one movement of at least one object through the background environment. The computing device may remove the image of the background environment from the first media stream to create a second media stream that includes the movement of the object without the image of the background environment. The computing device may determine a bandwidth of a network over which the second media stream will be transmitted and perform further alterations to the second media stream if the current bandwidth is less than a bandwidth threshold level in order to reduce the bandwidth needed to transmit the second media stream.

20 Claims, 5 Drawing Sheets

(51) Int. Cl.
*G06T 7/194* (2017.01)
*H04L 12/927* (2013.01)
*G16H 40/67* (2018.01)

(52) U.S. Cl.
CPC ........ *H04L 65/4084* (2013.01); *H04L 65/601* (2013.01); *G06T 2207/10021* (2013.01); *G16H 40/67* (2018.01)

(58) Field of Classification Search
USPC ........................................................ 709/231
See application file for complete search history.

(56) References Cited

U.S. PATENT DOCUMENTS

| | | | |
|---|---|---|---|
| 7,339,993 B1 | 3/2008 | Brooks et al. | |
| 7,571,246 B2 | 8/2009 | Virdi et al. | |
| 8,307,395 B2 | 11/2012 | Issa et al. | |
| 8,655,093 B2 * | 2/2014 | El Dokor | G06K 9/34 382/254 |
| 8,787,454 B1 | 7/2014 | Chechik et al. | |
| 8,922,665 B2 * | 12/2014 | Cooper | H04N 1/00204 348/211.6 |
| 9,460,522 B2 * | 10/2016 | Saitwal | G06T 7/215 |
| 9,465,994 B1 * | 10/2016 | Mishra | G06K 9/00791 |
| 10,026,509 B2 | 7/2018 | Powers et al. | |
| 2003/0020683 A1 | 1/2003 | Waterman | |
| 2004/0045030 A1 | 3/2004 | Reynolds et al. | |
| 2004/0218827 A1 | 11/2004 | Cohen et al. | |
| 2005/0018768 A1 | 1/2005 | Mabey et al. | |
| 2007/0047650 A1 | 3/2007 | Vilei et al. | |
| 2008/0109865 A1 | 5/2008 | Su et al. | |
| 2009/0016603 A1 * | 1/2009 | Rossato | G06T 7/194 382/173 |
| 2011/0305150 A1 | 12/2011 | Haver et al. | |
| 2012/0265737 A1 | 10/2012 | Potkonjak | |
| 2013/0121563 A1 * | 5/2013 | Chen | H04N 19/29 382/154 |
| 2014/0023199 A1 | 1/2014 | Giesbrecht | |
| 2014/0130115 A1 | 5/2014 | Losev et al. | |
| 2014/0143439 A1 * | 5/2014 | Ramamurthy | H04N 21/2407 709/231 |
| 2014/0153773 A1 | 6/2014 | Gupta et al. | |
| 2014/0169450 A1 | 6/2014 | Wahadaniah et al. | |
| 2014/0233637 A1 | 8/2014 | Saleem et al. | |
| 2014/0244247 A1 | 8/2014 | Christensen et al. | |
| 2015/0156555 A1 | 6/2015 | Putterman et al. | |
| 2015/0281715 A1 * | 10/2015 | Lawrence | G06T 7/215 375/240.16 |
| 2015/0288933 A1 * | 10/2015 | Iversen | G06F 1/163 348/14.07 |
| 2017/0035330 A1 * | 2/2017 | Bunn | A61B 5/1128 |
| 2017/0149608 A1 | 5/2017 | Freimuth et al. | |
| 2017/0251515 A1 | 8/2017 | Altman et al. | |
| 2018/0139254 A1 * | 5/2018 | Oyman | H04L 67/2842 |
| 2018/0144476 A1 * | 5/2018 | Smith | G06T 3/40 |
| 2018/0146019 A1 * | 5/2018 | Chen | H04L 65/4069 |
| 2018/0262714 A1 * | 9/2018 | Kim | H04N 7/147 |
| 2018/0286053 A1 * | 10/2018 | Labbe | H04N 19/597 |
| 2019/0104331 A1 | 4/2019 | Bapna et al. | |
| 2019/0149867 A1 | 5/2019 | Singh et al. | |
| 2019/0173929 A1 | 6/2019 | Guardini et al. | |

OTHER PUBLICATIONS

Curcio et al., 2017. Bandwidth Reduction of Omnidirectional Viewport-Dependent Video Streaming via Subjective Quality Assessment. In Proceedings of the 2nd International Workshop on Multimedia Alternate Realities (AltMM '17). Association for Computing Machinery, NY, NY, p. 9-14 (Year: 2017).*

U.S. Appl. No. 16/952,981, filed Nov. 19, 2020, filed by Mitchell et al.

Poropatich, "TATRC's Strategy for the Research and Development of Mobile Health Applications", retrieved from the internet http://reboot.fcc.gov/c/document_library/get_file?iuid=8ac18153-1b96-4e14-958c-9538a7fc272c&groupId=19001, Jul. 26, 2010, 12 pp.

Gilbert, "First Responder Medical Information Exchange and Telemedicine over Tactical Radio Networks", retrieved from the internet, http://www.abstractsonline.com/plan/ViewAbstract.aspx?mID=2885&sKey=7fc33465-d67b-4f60-a795-fc877c8cfdb9&cKey=a647460e-6ae3-4131-9429-bb4123a501e0&mKey=%7B36FB8B6A-932F-4EDB-A20A-A9448F2863D0%7D, retrieved on May 6, 2016, 3pp.

Shenai, et al., "Virtual interactive presence and augmented reality (VIPAR) for remote surgical assistance", retrieved from the internet, http://www.ncbi.nlm.nih.gov/pubmed/21304333, Mar. 2011, 2pp.

"Maintenance Analytics to Generate $24.7 Billion in 2019, Driven by Predictive Maintenance and Internet of Things," ABIresearch, Mar. 28, 2014, accessed from https://www.abiresearch.com/press/maintenance-analytics-to-generate-247-billion-in-2/, 2 pp.

Tegtmeier et al., "Fleet Retirements Heavily $56 Billion MRO Market," AviationWeek, accessed from http://aviationweek.com/print/mro/fleet-retirements-heavily-56-billion-mro-market, Apr. 17, 2013, 2 pp.

Monegain et al., "Telemedicine market to soar past $30B," Healthcare IT News, accessed from http://www.healthcareitnews.com/news/telemedicine-poised-grow-big-time, Aug. 4, 2015, 21 pp.

SBIR STIR America's Seed Fund, "TEL TAN: TELemedcine over a TActical Network", Award Year: 2015, retrieved from the internet https://lwww.sbir.gov/sbirsearch/detail/869291, retrieved on May 26, 2016, 2 pp.

Prosecution History from U.S. Appl. No. 15/174,704, dated Jun. 6, 2016 through Apr. 26, 2018, 114 pp.

U.S. Appl. No. 16/432,457, filed Jun. 5, 2019, by Tyler J. Mitchell et al.

Prosecution History from U.S. Appl. No. 16/015,116, dated Sep. 4, 2018 through Jun. 26, 2020, 96 pp.

Prosecution History from U.S. Appl. No. 16/432,457, dated Jun. 9, 2020 through Sep. 2, 2020, 28 pp.

U.S. Appl. No. 16/015,116, filed Jun. 21, 2018, by Tyler J. Mitchell et al.

* cited by examiner

US 11,245,743 B1

BANDWIDTH DEPENDENT MEDIA STREAM COMPRESSION

This application is a continuation of U.S. application Ser. No. 16/015,116, filed Jun. 21, 2018, which issued as U.S. Pat. No. 10,812,562 on Oct. 20, 2020, the entire content of which is incorporated herein by reference.

STATEMENT REGARDING FEDERALLY SPONSORED RESEARCH OR DEVELOPMENT

This invention was made with government support under Contract No. W81XWH-15-C-0161 and Contract No. W81XWH-16-C-0195 awarded by the US Army. The government has certain rights in this invention.

TECHNICAL FIELD

The disclosure relates to capturing, editing, and transmitting media streams.

BACKGROUND

In general, digital image editing techniques are complicated, processing-heavy techniques where the edited images require more blocks of a storage device than the original image. Further, digital image editing tends to require an abundance of user input to edit an image to the user's liking. This issue is only exacerbated when applied to video editing, as edits must be made to each frame unless a universal edit, such as a color scheme change, is made.

One example where image editing techniques may be applied is with a combat medic in a battlefield. Combat medics can quickly be overcome with the variety and number of injuries received by fellow warfighters. Warfighters are being pushed further and further afield, leaving them outside the range of medical experts. Virtual Interactive Presence and Augmented Reality (VIPAR) systems already in place have shown great potential in alleviating these problems, but these system require too many prerequisites to use in the field. Expensive and specialized pieces of hardware are an additional strain on warfighters, and often times require supplemental training. Systems designed and tested on broadband speed, high fidelity networks are unsuitable for the tumultuous nature of a joint tactical radio system (JTRS) network.

SUMMARY

In general, this disclosure describes media stream transmission techniques for a field computing device and a central computing device. For instance, a central computing device may capture an image of a background environment, wherein the background environment is local to the central computing device. The central computing device may then record a first media stream, where the first media stream includes at least a portion of the image of the background environment, and where the first media stream further includes a representation of at least one movement of at least one object through the background environment. The central computing device may then remove the image of the background environment from the first media stream to create a second media stream, where the second media stream includes the representation of the at least one movement of the at least one object without the image of the background environment. The central computing device may then determine a current bandwidth level of a network over which the second media stream will be transmitted. The central computing device may compare the current bandwidth level to a bandwidth threshold associated with the second media stream. Responsive to determining that the current bandwidth level of the network is less than the bandwidth threshold, the central computing device may alter the second media stream to reduce an amount of data transmitted in the second media stream. After altering the second media stream, the central computing device may transmit the second media stream to the field computing device via the network.

In one example, the disclosure is directed to a method comprising capturing, by a central computing device, an image of a background environment, wherein the background environment is local to the central computing device, recording, by the central computing device, a first media stream, wherein the first media stream includes at least a portion of the image of the background environment, and wherein the first media stream further includes a representation of at least one movement of at least one object through the background environment, removing, by the central computing device, the image of the background environment from the first media stream to create a second media stream, wherein the second media stream includes the representation of the at least one movement of the at least one object without the image of the background environment, determining, by the central computing device, a current bandwidth level of a network over which the second media stream will be transmitted, comparing, by the central computing device, the current bandwidth level to a bandwidth threshold associated with the second media stream, responsive to determining that the current bandwidth level of the network is less than the bandwidth threshold, altering, by the central computing device, the second media stream to reduce an amount of data transmitted in the second media stream, and after altering the second media stream, transmitting, by the central computing device and to a field computing device via the network, the second media stream.

In another example, the disclosure is directed to a device comprising a camera, at least one processor, and a storage device configured to store one or more modules operable by the at least one processor to capture an image of a background environment, wherein the background environment is local to the central computing device, record a first media stream, wherein the first media stream includes at least a portion of the image of the background environment, and wherein the first media stream further includes a representation of at least one movement of at least one object through the background environment, remove the image of the background environment from the first media stream to create a second media stream, wherein the second media stream includes the representation of the at least one movement of the at least one object without the image of the background environment, determine a current bandwidth level of a network over which the second media stream will be transmitted, compare the current bandwidth level to a bandwidth threshold associated with the second media stream, responsive to determining that the current bandwidth level of the network is less than the bandwidth threshold, alter the second media stream to reduce an amount of data transmitted in the second media stream, and after altering the second media stream, transmit, to a field computing device via the network, the second media stream.

In another example, the disclosure is directed to an apparatus comprising means for capturing an image of a background environment, wherein the background environment is local to the apparatus, means for recording a first media stream, wherein the first media stream includes at least a portion of the image of the background environment, and wherein the first media stream further includes a representation of at least one movement of at least one object through the background environment, means for removing the image of the background environment from the first media stream to create a second media stream, wherein the second media stream includes the representation of the at least one movement of the at least one object without the image of the background environment, means for determining a current bandwidth level of a network over which the second media stream will be transmitted, means for comparing the current bandwidth level to a bandwidth threshold associated with the second media stream, means for altering the second media stream to reduce an amount of data transmitted in the second media stream in response to determining that the current bandwidth level of the network is less than the bandwidth threshold, and means for transmitting, to a field computing device via the network, the second media stream after altering the second media stream.

In another example, the disclosure is directed to a computer-readable medium storing instructions that, when executed, cause one or more processors of a central computing device to capture an image of a background environment, wherein the background environment is local to the central computing device, record a first media stream, wherein the first media stream includes at least a portion of the image of the background environment, and wherein the first media stream further includes a representation of at least one movement of at least one object through the background environment, remove the image of the background environment from the first media stream to create a second media stream, wherein the second media stream includes the representation of the at least one movement of the at least one object without the image of the background environment, determine a current bandwidth level of a network over which the second media stream will be transmitted, compare the current bandwidth level to a bandwidth threshold associated with the second media stream, responsive to determining that the current bandwidth level of the network is less than the bandwidth threshold, alter the second media stream to reduce an amount of data transmitted in the second media stream, and after altering the second media stream, transmit, to a field computing device via the network, the second media stream.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
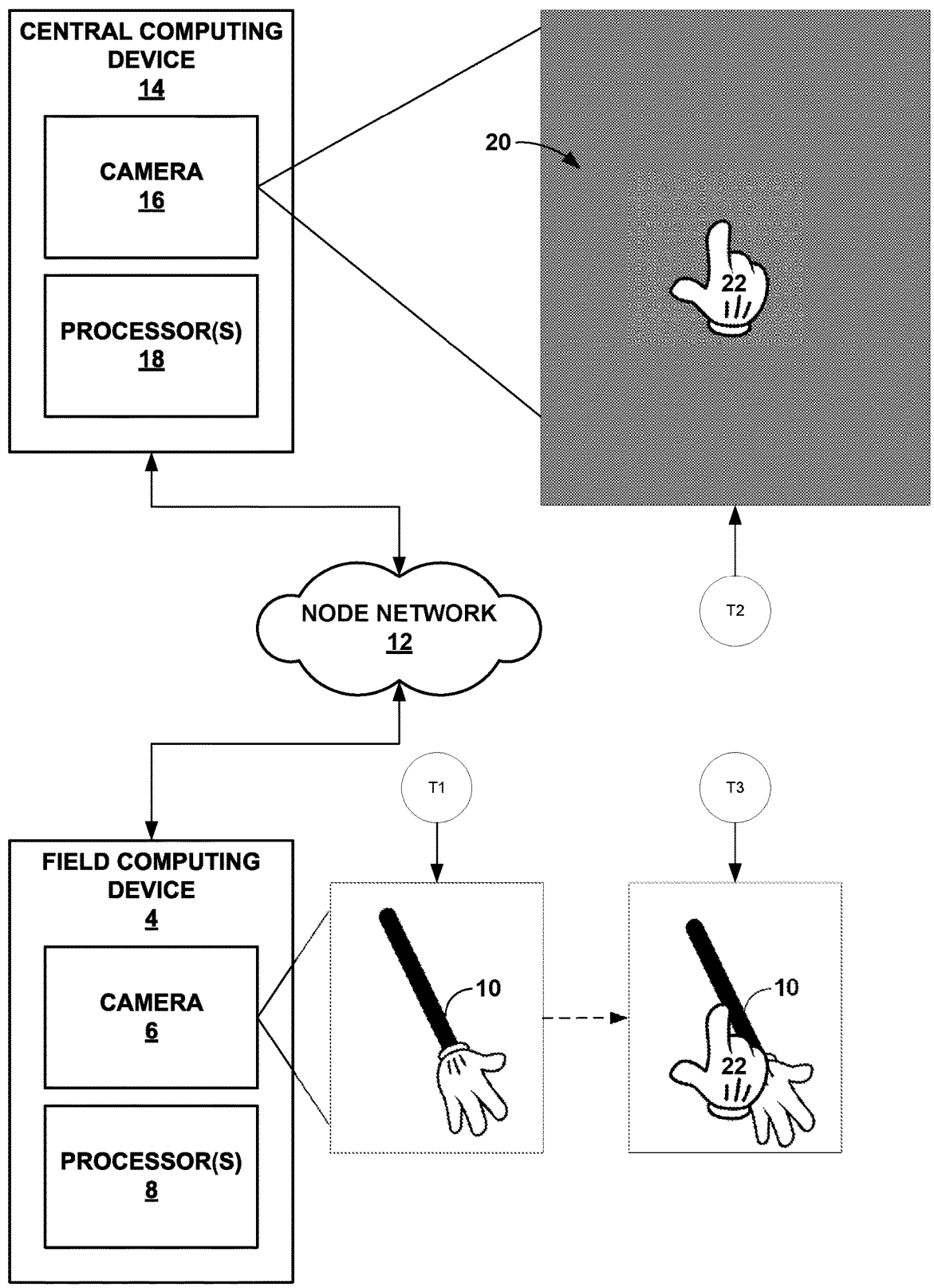
FIG. 1 is a block diagram illustrating an example of media stream transmissions between a field computing device and a central computing device, in accordance with one or more techniques of this disclosure.

In general, this disclosure describes an improved system for transmitting media streams in a low-bandwidth environment between a field computing device and a central computing device. This subject matter was initially described in U.S. patent application Ser. No. 15/174,704, filed Jun. 6, 2016, which issued as U.S. Pat. No. 10,026,509 on Jul. 17, 2018, and which claims the benefit of U.S. Provisional Application No. 62/269,838, filed Dec. 18, 2015, the entire content of each of which are incorporated herein in their entirety. In many instances, media stream transmissions must over networks that can only transmit data packets with a low bandwidth. As such, sending a full media stream over such a network can be slow and lead to dropped packets during the transmission. As one non-limiting example, if a field medic requires assistance from a remote expert, the expert would typically move themselves or a pointer object in front of a green screen such that the expert may point to portions of a received video containing an injury. However, the full video of the pointer object and the received media stream may need to be sent to the field medic, incurring delays from a large file transmission over the low-bandwidth network. When a field medic requires assistance, any delay or missing portions of an instruction video may lead to further health deterioration. For the purposes of this disclosure, a media stream may be any transmission of data between two computing devices. For instance, a media stream may include video data. In other instances, a media stream may, further or alternatively, include image data, audio data, or textual data. For example, a media stream may include video data and textual data corresponding to a heart rate and a blood pressure.

In cases such as these, for example, the ability for a medical expert to see medical problems in real time, and offer assistance based on what the expert sees, may assist in saving numerous lives. Virtual Interactive Presence and Augmented Reality (VIPAR) systems offer a possible solution to this. However, existing VIPAR systems have a number of flaws. Expensive and specialized hardware is the highest bar of entry for existing VIPAR systems. For instance, loading warfighters with additional hardware that requires special precautions in transit makes current systems difficult to deploy. Existing VIPAR systems further require low-latency, high-bandwidth networks to function properly. Tactical networks, on the other hand, may have limited bandwidth with high latency and intermittent loss of service. The practical limitations of tactical networks mean that an application may need to be developed with these limitations in mind. Otherwise, the resulting video stream may be delayed, choppy, and nonfunctional. Traditionally, video overlay systems require a flat background color in order to capture the correct image, which is rarely an option in the field, and even when it is possible to achieve, it can require extensive preparation time to set up. Further problems with hardware, bandwidth, and video systems have made adoption of VIPAR systems in the field very difficult.

In accordance with techniques of this disclosure, a central computing device may remove background images from a video, leaving only the portion of the original media stream that contains the pointer object moving through the environment. The altered media stream may include timing information such that the field computing device can locally superimpose the altered media stream on top of the initial media stream captured by the field computing device that is already stored on the field computing device itself. By performing this operation locally, the field computing device is not constrained by the low-bandwidth network. By cutting the size of the file being transmitted across the network, the transmission may be more efficiently and completely delivered.

This transmission system can be utilized for telemedicine over a tactical network (TELTAN). As described herein, TELTAN is a multi-platform VIPAR system emphasizing operation in low-fidelity networks, with low-bandwidth overhead. By operating with a low-bandwidth overhead, TELTAN may provide efficiency when run on a tactical network. A simple interface may allow for easy set up and connections, even under extreme conditions. Being deployable across multiple systems may remove the necessity for specialized hardware, and the easy-to-follow interface may require minimal training, lowering monetary costs, as well as easing field deployment. Organizations like civilian hospitals may benefit from immediate access to an expert, or emergencies in isolated areas where medical attention is out of immediate reach. Additionally, remote repairs of specialized hardware may be far more easily managed, rather than having to send an expert to the field.

Techniques of this disclosure may provide a video streaming system that allows a video stream to be sent to, e.g., an expert who can place their hands into the video stream, which is then sent back to the source. These techniques may be used over low-bandwidth, low-fidelity networks and run with low-system requirements, including on tablet computers and mobile phones. These techniques may produce quality images provided by onboard devices, like mobile phone cameras. Further, techniques of this disclosure do not have a Chroma Key (e.g., green screen or other) requirement, which may not always be an option in the field.

In various examples, a device carried by a warfighter in the field may be referred to as the "field computing device", and a device held by the expert, kept at a base of operations, may be referred to as the "central computing device." The field and central computing devices will connect, allowing for video captured by the field device to be streamed to the central computing device. Upon receiving the video, the expert may be able to "insert" their hands into the video stream. Information about the hands will then be sent back to the field computing device.

FIG. 1 is a block diagram illustrating an example of media stream transmissions between a field computing device 4 and a central computing device 14, in accordance with one or more techniques of this disclosure. Field computing device 4 is described below, for purposes of illustration only, as a smartphone. However, in some examples, field computing device 4 may be a computerized watch (e.g., a smart watch), computerized eyewear, computerized headwear, other types of wearable computing devices, a tablet computer, a personal digital assistant (PDA), a laptop computer, a gaming system, a media player, a television platform, an automobile navigation system, a digital camera, or any other type of mobile and/or non-mobile computing device that is configured to perform a media operation as described herein.

Field computing device 4 may include an input component. For instance, field computing device 4 may be configured to receive input from a user through tactile, audio, or video feedback. Examples of input components include a display component, a mouse, a keyboard, a camera, a microphone or any other type of device for detecting input from a user. In some examples, a display component includes a touch-sensitive screen. Field computing device 4 may also include a structure capable of receiving a radio signal. For instance, field computing device 4 may include a radio antenna, a radio receiver, a communication receiver, or a scanner, among other things. In the non-limiting example of FIG. 1, field computing device 4 includes camera 6, which may be configured to capture moving images, still images, and, in some instances where camera 6 includes a microphone, audio data.

Field computing device 4 may further include one or more processors 8. One or more processors 8, in one example, are configured to implement functionality and/or process instructions for execution within field computing device 4. For example, processors may be capable of processing instructions stored in a storage device of field computing device 4. Examples of processors 8 may include, any one or more of a microprocessor, a controller, a digital signal processor (DSP), an application specific integrated circuit (ASIC), a field-programmable gate array (FPGA), or equivalent discrete or integrated logic circuitry.

Central computing device 14 is described below as a desktop computer. However, in some examples, central computing device 14 may be a smartphone, a computerized watch (e.g., a smart watch), computerized eyewear, computerized headwear, other types of wearable computing devices, a tablet computer, a personal digital assistant (PDA), a laptop computer, a gaming system, a media player, an e-book reader, a television platform, an automobile navigation system, a digital camera, or any other type of mobile and/or non-mobile computing device that is configured to perform a media operation as described herein.

Central computing device 14 may include an input component. For instance, central computing device 14 may be configured to receive input from a user through tactile, audio, or video feedback. Examples of input components include a display component, a mouse, a keyboard, a camera, a microphone or any other type of device for detecting input from a user. In some examples, a display component includes a touch-sensitive screen. Central computing device 14 may also include a structure capable of receiving a radio signal. For instance, central computing device 14 may include a radio antenna, a radio receiver, a communication receiver, or a scanner, among other things. In the example of FIG. 1, central computing device 14 includes camera 16, which may be configured to capture moving images, still images, and, in some instances where camera 16 includes a microphone, audio data.

Central computing device 14 may further include one or more processors 18. One or more processors 18, in one example, are configured to implement functionality and/or process instructions for execution within central computing device 14. For example, processors may be capable of processing instructions stored in a storage device of central computing device 14. Examples of processors 18 may include, any one or more of a microprocessor, a controller, a digital signal processor (DSP), an application specific integrated circuit (ASIC), a field-programmable gate array (FPGA), or equivalent discrete or integrated logic circuitry.

Field computing device 4 and central computing device 14 may be capable of sending media transmissions across node network 12. Node network 12 may represent any communication network, such as a packet-based digital network. In other examples, node network 12 may represent any wired or wireless network such as the Internet, a private corporate intranet, or a PSTN telephonic network. Node network 12 may include both wired and wireless networks as well as both public and private networks. Field computing device 4 and central computing device 14 may each contain one or more devices for accessing node network 12, such as modems, switches and the like. Network access devices (e.g., a router and firewall) may couple the private network to node network 12 for communication with computing devices associated with central computing device 14. In some examples, node network 12 may include a system of interconnected radio towers that receive a media stream from field computing device 4, send the media stream to one or more other radio towers, and, ultimately, forward the media stream to central computing device 14.

In accordance with techniques of the current disclosure, at time Ti, field computing device 4 may capture a first media stream. The first media stream includes timing information. The timing information may include a time that the media stream begins, such as a time of day or a 0:00:00 indication, and a time that the media stream ends, such as a time of day later than the first time of day or a time in the form of #:##:##, wherein the #'s indicate numbers describing the length of the first media stream. The first media stream may include object 10, which may, in certain non-limiting examples, be a body part containing an injury or an ailment that is to be treated medically. In the example of FIG. 1, object 10 is a subject's arm that may, for instance, be dislocated. Field computing device 4 may send the first media stream to central computing device 14 across node network 12.

Central computing device 14 may receive the first media stream at a remote location, where a medical expert may analyze the injury and determine a medical treatment that must be performed on object 10. To respond, central computing device 14 may first capture an image of background environment 20. Background environment 20 may be local to central computing device 14. Background environment 20 may be any background environment, such as a solid-colored or patterned background "stage" or a general room containing various objects, among other things.

Central computing device 14 may record a second media stream. The second media stream may include at least a portion of the image of background environment 20 and at least one movement of object 22 (e.g., image of the medical expert's hand) through background environment 20. For instance, after analyzing the injury to object 10, a medical expert may determine that a portion of object 10 may need to be moved or set in a specific manner, or that medical treatment must be provided to a specific portion of object 10. In the example of FIG. 1, where the subject's arm is dislocated, object 22 may move in a way that corresponds to the movement that must occur to re-set the subject's arm into the correct socket and how to prepare a sling for the arm to be cradled until further medical treatment can be provided.

Central computing device 14 may remove the image of background environment 20 from the second media stream to create a third media stream. The third media stream, accordingly, may only include the at least one movement of object 22 through background environment 20 without actually including the image of background environment 20. By removing the image of background environment 20, the third media stream will have a smaller size than the second media stream, allowing it to cross low-bandwidth node network 12 quicker and more efficiently.

The image of background environment 20 may be removed in any way suitable for the techniques described herein. For instance, if background environment 20 is a solid color, central computing device 14 may remove any pixel from the second media stream that matches or approximately matches (taking into account shading) the color of the pixels in the image of background environment 20. If background environment 20 is a patterned background or a general room, the color-removal process may be repeated for each color found in the image of background environment 20. In other examples, central computing device 14 may compute a depth at which background environment 20 lies in the image of background environment 20. Central computing device 14 may then remove all objects from the second media stream found at that depth, leaving only the newly introduced object 22 in the third media stream. These are merely examples of how background environment 20 may be removed from the third media stream. Any other technique available that results in the removal of background environment 20 from the second media stream may be utilized in accordance with the techniques of the current disclosure.

For instance, in another example of removing the image of background environment 20 from the second media stream, central computing device 14 may store a set of one or more object patterns. Each object pattern in the set of one or more object patterns may be one of a possible shape or a possible color of a possible configuration of the at least one object. Central computing device 14 may determine one or more portions of the first media stream that match an object pattern of the set of one or more object patterns. For each frame of the at least one frame of the first media stream, central computing device 14 may remove each pixel of the first media stream that is outside of the one or more portions that match the object pattern. For example, central computing device 14 may store different possible shapes and colors of hands. Central computing device 14 may attempt to find a portion of the second media stream that matches one of the object patterns containing possible shapes and colors of hands. Determining that the found portion is a hand, central computing device 14 may remove the pixels in the second media stream that are outside of the found portion, leaving only the hand in the second media stream.

In another example of removing the image of background environment 20 from the second media stream, central computing device 14 may, for each frame of at least one frame of the second media stream, compare the respective frame of the first media stream to the image of the background environment. Central computing device 14 may then remove each pixel of the second media stream with a color value equal to a color value of a corresponding pixel value in the image of the background environment. For instance, if camera 16 is in a fixed position, the background environment will not change between the image of the background environment and the filming of the second media stream. As such, if object 22 is in the middle of the second media stream, the pixel in the top-left corner of the second media stream may have a color value equal to the pixel in the top-left corner of the image of the background environment. As such, this pixel may be removed. Removing each matching pixel from each frame of the second media stream may leave only object 22 in the second media stream.

Central computing device 14, operating in a generally low-bandwidth environment, may perform further operations to reduce the bandwidth needed to efficiently send the third media stream to field computing device 4. While the environment of node network 12 is generally a low-bandwidth environment, if the available bandwidth on node network 12 falls below a certain level, central computing device 14 may perform additional operations to ensure that central computing device 14 transmits the second media stream in an efficient manner. For instance, central computing device 14 may determine a current bandwidth level of node network 12 over which the third media stream will be transmitted. Central computing device 14 may then compare the current bandwidth level to a bandwidth threshold associated for node network 12. In some instances, the bandwidth threshold may be a static value for the particular network or a particular environment that the network is situated in, either set by an administrator or automatically set based on various network characteristics of the network. In other instances, the bandwidth threshold may be dynamically set based on characteristics of the third media stream, central computing device 14, and/or field computing device 4. For instance, certain devices may require a certain minimum bandwidth in order to operate effectively. As another example, central computing device 14 may set the bandwidth threshold based on the size of the third media stream (e.g., such that, given the size of the third media stream, central computing device 14 is able to fully send the third media stream within a particular amount of time). For instance, if the third media stream is 10000 Kilobytes (KB) in size, and the system is set to fully transmit the second media stream within 2 minutes, central computing device 14 may set the bandwidth threshold to equal 83.3 KB/sec. In still other examples, such as in a live streaming situation, the bandwidth threshold may be set such that field computing device 4 is able to receive and play the third media stream at at least a minimum quality level (e.g., without skipping or buffering, or at a particular frames per second rate).

Responsive to determining that the current bandwidth level of the network is less than the bandwidth threshold, central computing device 14 may alter the second media stream to reduce an amount of data transmitted in the second media stream. In reducing the file size, central computing device 14 may do so to an extent that central computing device 14 may effectively and efficiently transmit the second media stream according to the parameters of the network (e.g., within a particular time limit given the available bandwidth, etc.).

Central computing device 14 may include timing information in the third media stream such that the timing information of the third media stream can be synchronized to the timing information of the first media stream. The timing information may include a time corresponding to the time that the first media stream begins, such as the time of day or the 0:00:00 indication, and a time corresponding to the time that the first media stream ends, such as the time of day later than the first time of day or the time in the form of #:##:##, wherein the #'s indicate numbers describing the length of the first media stream.

At time T3, field computing device 4 may receive, from central computing device 14, the third media stream. As described above, the third media stream may include at least one movement of object 22 without any images of background environment 20. The third media stream may further include timing information corresponding to the timing information of the first media stream.

Field computing device 4, with the received third media stream and the originally captured first media stream, may superimpose the received third media stream on the first media stream. Field computing device 4 may perform the superimposing based at least in part on synchronizing the timing information of the third media stream with the timing information of the first media stream. For instance, if the timing information of the third media stream includes a start time in an hour-minute-second #:##:## format, field computing device 4 may superimpose the third media stream on top of the first media stream at a point in the first media stream that equals the start time of the third media stream. For instance, the third media stream may start at 0:00:06, meaning six seconds into the first media stream. As such, at the six second mark of the first media stream, field computing device 4 may superimpose the third media stream on top of the first media stream, playing both media streams simultaneously until both media streams end. In some examples, when the third media stream contains audio, field computing device 4 may further replace any audio in the first media stream with the audio of the third media stream.

The superimposed video provides the field computing device with a treatment for object 10. For instance, in the example of FIG. 1, where object 10 is a dislocated arm, object 22 would be overlaid on top of object 10, and would appear to move along object 10 in a way necessary for treatment of the dislocated arm to occur, such as a movement to re-set the dislocated arm and to place the arm in a sling. By performing the superimposing locally on field computing device 4 rather than field computing device 4 receiving a full media stream of the treatment over low-bandwidth node network 12, field computing device 4 is able to receive a quality instructional treatment in a shorter time than if field computing device 4 waited for the entirety of a full media stream to be received.

Figure 2:
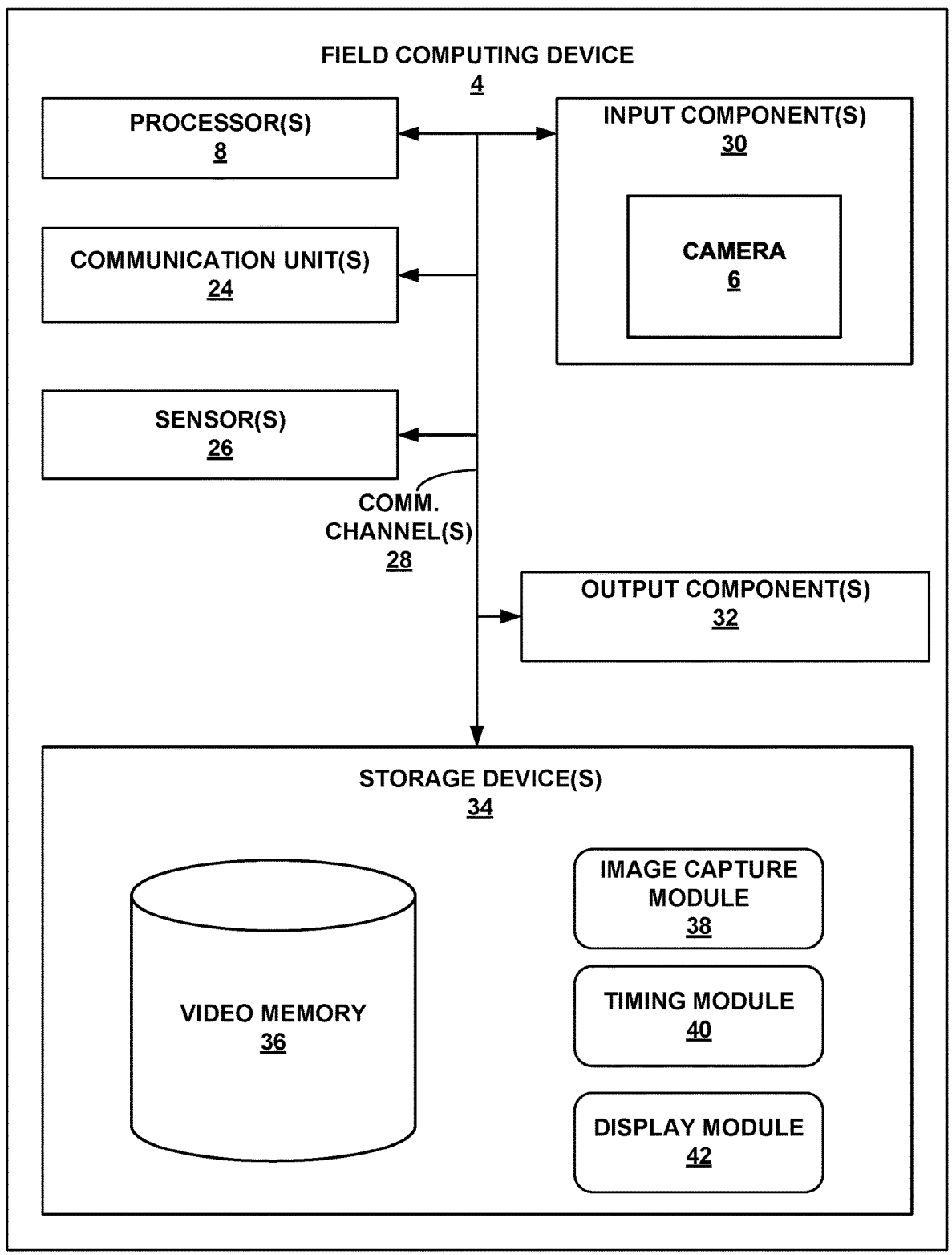
FIG. 2 is a block diagram illustrating an example field computing device, in accordance with one or more techniques of this disclosure.

FIG. 2 is a block diagram illustrating an example field computing device 4, in accordance with one or more techniques of this disclosure. Field computing device 4 of FIG. 2 is described below as one particular example of field computing device 4 shown in FIG. 1. FIG. 2 illustrates only one particular example of field computing device 4, and many other examples of field computing device 4 may be used in other instances and may include a subset of the components included in example field computing device 4 or may include additional components not shown in FIG. 2.

For example, field computing device 4 may include a battery to provide power to the components of field computing device 4. Similarly, the components of field computing device 4 shown in FIG. 2 may not be necessary in every example of field computing device 4. For example, in some configurations, field computing device 4 may not include communication units 24.

As shown in the example of FIG. 2, field computing device 4 includes one or more processors 8, one or more input components 30, one or more communication units 24, one or more output components 32, one or more sensors 26, and one or more storage devices 34. Input components 30 may include camera 6.

Output components 32, in some examples, are configured to provide output to a user using tactile, audio, or video stimuli. Output components 32, in one example, include an electronic display, a loudspeaker, or any other type of device for converting a signal into an appropriate form understandable to humans or machines. The electronic display may be a liquid crystal display (LCD) or organic light-emitting diode (OLED) part of a touch screen, may be a non-touchscreen direct view display component such as a cathode ray tube (CRT), light-emitting diode (LED), LCD, or OLED. The display component may also be a projector instead of a direct view display.

Input components 30, in some examples, is configured to receive input from a user through tactile, audio, or video feedback. Examples of input components 30 include a display component, a mouse, a keyboard, a camera, a microphone or any other type of device for detecting input from a user. In some examples, a display component includes a touch-sensitive screen. Input component 30 may, for instance, include camera 6. In some instances, camera 6 may be configured to record an image or a video stream. In some further instances, camera 6 may also include a microphone to capture audio data.

One or more storage devices 34 of field computing device 4 include video memory 36, image capture module 38, timing module 40, and display module 42. One or more storage devices 34 may be configured to store information within field computing device 4 during operation. Storage device 34, in some examples, is described as a computer-readable storage medium. In some examples, storage device 34 and video memory 36 is a temporary memory, meaning that a primary purpose of storage device 34 and video memory 36 is not long-term storage. Storage device 34 and video memory 36, in some examples, are described as volatile memories, meaning that storage device 34 and video memory 36 do not maintain stored contents when the computing device is turned off. Examples of volatile memories include random access memories (RAM), dynamic random access memories (DRAM), static random access memories (SRAM), and other forms of volatile memories known in the art. In some examples, storage device 34 is used to store program instructions for execution by processors 8.

Storage devices 34 and video memory 36, in some examples, also include one or more computer-readable storage media. Storage devices 34 and video memory 36 may be configured to store larger amounts of information than volatile memory. Storage devices 34 and video memory 36 may further be configured for long-term storage of information. In some examples, storage devices 34 and video memory 36 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Communication channels 28 may interconnect each of the components 8, 24, 26, 30, 6, 32, 34, 36, 38, 40, and 42 for inter-component communications (physically, communicatively, and/or operatively). In some examples, communication channels 28 may include a system bus, a network connection, an inter-process communication data structure, or any other method for communicating data.

One or more communication units 24 of field computing device 4 may communicate with external devices, such as a server device, via one or more wired and/or wireless networks by transmitting and/or receiving network signals on the one or more networks. Communication units 24 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, field computing device 4 utilizes communication units 24 to wirelessly communicate with another computing device that is operably coupled to field computing device 4, such as central computing device 14 of FIG. 1.

One or more processors 8, in one example, are configured to implement functionality and/or process instructions for execution within field computing device 4. For example, processors 8 may be capable of processing instructions stored in storage device 34. Examples of processors 8 may include, any one or more of a microprocessor, a controller, a digital signal processor (DSP), an application specific integrated circuit (ASIC), a field-programmable gate array (FPGA), or equivalent discrete or integrated logic circuitry.

In some examples, field computing device 4 may include one or more sensors 26. One or more of sensors 26 may measure one more measurands. Examples of one or more of sensors 26 may include one or more position sensors (e.g., a global positioning system (GPS) sensor, an indoor positioning sensor, or the like), one or more motion/orientation sensors (e.g., an accelerometer, a gyroscope), a light sensor, a temperature sensor, a pressure (or grip) sensor, a physical switch, a proximity sensor, and one or more bio-sensors that can measure properties of the skin/blood, such as alcohol, blood sugar, heart rate, and/or perspiration level.

In accordance with techniques of the current disclosure, image capture module 38 of field computing device 4 may capture a first media stream and store the first media stream in video memory 36. The first media stream includes timing information. The timing information may include a time that the media stream begins, such as a time of day or a 0:00:00 indication, and a time that the media stream ends, such as a time of day later than the first time of day or a time in the form of #:##:##, wherein the #'s indicate numbers describing the length of the first media stream. The first media stream may include representation of an object, which may, in certain non-limiting examples, be a body part containing an injury or an ailment that is to be treated medically. In the example of FIG. 2, for purposes of description only, the object may be a subject's leg that may, for instance, be gashed. Image capture module 38 of field computing device 4 may send the first media stream to a central computing device (e.g., central computing device 14 of FIG. 1) across a node network (e.g., node network 12 of FIG. 1).

Field computing device 4 may receive, from the central computing device, a second media stream. The second media stream may include at least one movement of a second object without any images of a background environment. The second media stream may further include timing information corresponding to the timing information of the first media stream.

Display module 42 of field computing device 4, with the received second media stream and the originally captured first media stream stored in video memory 36, may superimpose the received second media stream on the first media stream. Display module 42 of field computing device 4 may perform the superimposing based at least in part on timing module 40 aligning the timing information of the second media stream with the timing information of the first media stream. For instance, if the timing information of the second media stream includes a start time in an hour-minute-second #:##:## format, display module 42 may superimpose the second media stream on top of the first media stream at a point in the first media stream that equals the start time of the second media stream, as determined by timing module 40. For instance, timing module 40 may determine that the second media stream may start at 0:00:06, meaning six seconds into the first media stream. As such, at the six second mark of the first media stream, display module 42 may superimpose the second media stream on top of the first media stream, playing both media streams simultaneously until both media streams end. In some examples, when the second media stream contains audio, display module 42 may further replace any audio in the first media stream with the audio of the second media stream.

In some examples, display module 42 may alter the size of the received second media stream. For instance, display module 42 may resize the received second media stream such that it is in the same aspect ratio as the recorded first media stream.

The superimposed video provides the field computing device with a treatment for object 10. For instance, where the first object is a gashed leg, the second object would be overlaid on top of the gashed leg, and would appear to move along the gashed leg in a way necessary for treatment of the gashed leg to occur, such as a movement to suture the wound. By performing the superimposing locally on field computing device 4 rather than field computing device 4 receiving a full media stream of the treatment over a low-bandwidth node network, field computing device 4 is able to receive a quality instructional treatment in a shorter time than if field computing device 4 waited for the entirety of a full media stream to be received.

Figure 3:
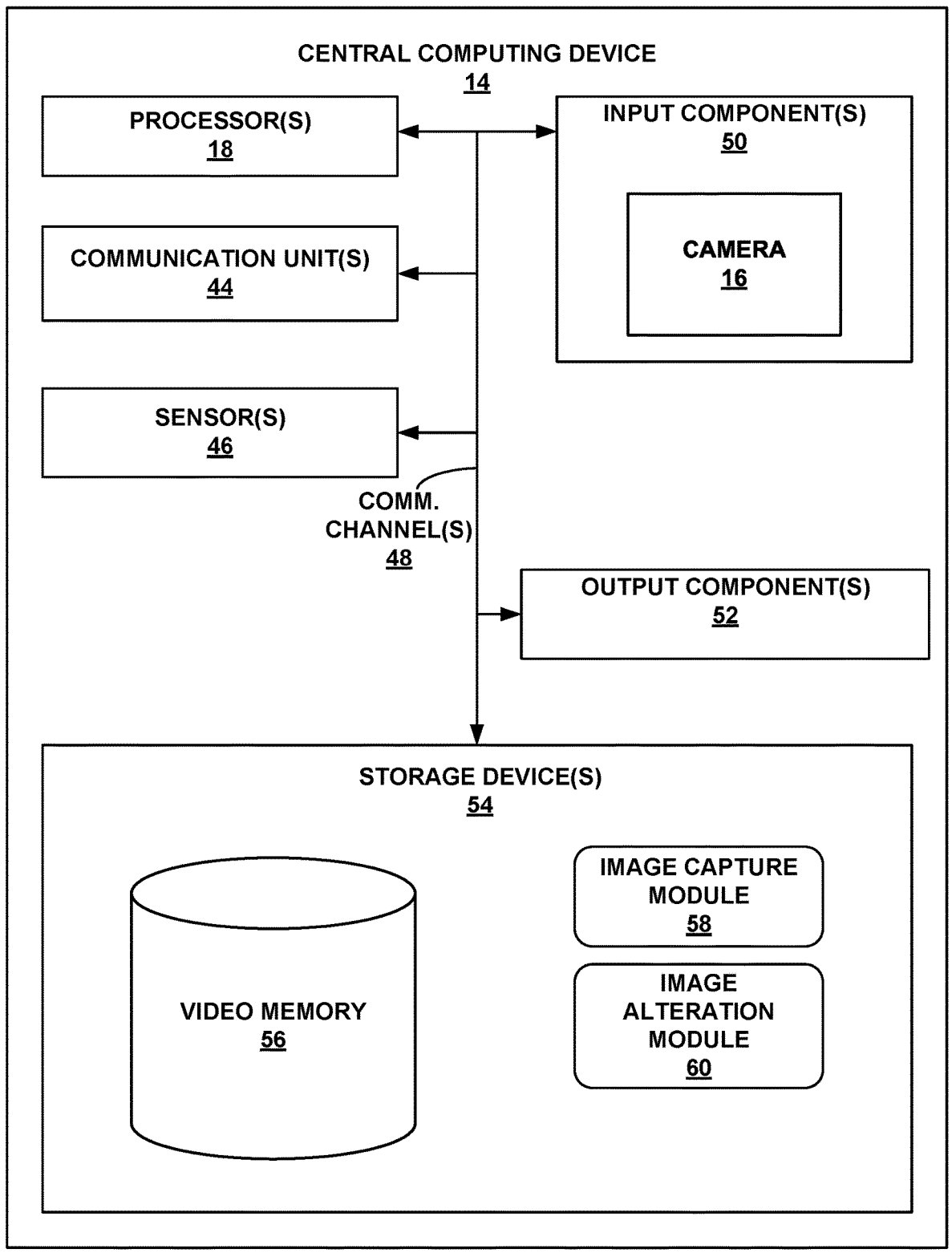
FIG. 3 is a block diagram illustrating an example central computing device, in accordance with one or more techniques of this disclosure.

FIG. 3 is a block diagram illustrating an example central computing device 14, in accordance with one or more techniques of this disclosure. Central computing device 14 of FIG. 3 is described below as one particular example of central computing device 14 shown in FIG. 1. FIG. 3 illustrates only one particular example of central computing device 14, and many other examples of central computing device 14 may be used in other instances and may include a subset of the components included in example central computing device 14 or may include additional components not shown in FIG. 3.

For example, central computing device 14 may include a battery to provide power to the components of central computing device 14. Similarly, the components of central computing device 14 shown in FIG. 3 may not be necessary in every example of central computing device 14. For example, in some configurations, central computing device 14 may not include communication units 44.

As shown in the example of FIG. 3, central computing device 14 includes one or more processors 18, one or more input components 50, one or more communication units 44, one or more output components 52, one or more sensors 46, and one or more storage devices 54. Input components 50 may include camera 16.

Output components 52, in some examples, are configured to provide output to a user using tactile, audio, or video stimuli. Output components 52, in one example, include an electronic display, a loudspeaker, or any other type of device for converting a signal into an appropriate form understandable to humans or machines. The electronic display may be an LCD or OLED part of a touch screen, may be a non-touchscreen direct view display component such as a CRT, LED, LCD, or OLED. The display component may also be a projector instead of a direct view display.

Input components 50, in some examples, is configured to receive input from a user through tactile, audio, or video feedback. Examples of input components 50 include a display component, a mouse, a keyboard, a camera, a microphone or any other type of device for detecting input from a user. In some examples, a display component includes a touch-sensitive screen. Input component 50 may, for instance, include camera 16. In some instances, camera 16 may be configured to record an image or a video stream. In some further instances, camera 16 may also include a microphone to capture audio data.

One or more storage devices 54 of central computing device 14 include video memory 56, image capture module 58, and image alteration module 60. One or more storage devices 54 may be configured to store information within central computing device 14 during operation. Storage device 54, in some examples, is described as a computer-readable storage medium. In some examples, storage device 54 and video memory 56 is a temporary memory, meaning that a primary purpose of storage device 54 and video memory 56 is not long-term storage. Storage device 54 and video memory 56, in some examples, are described as volatile memories, meaning that storage device 54 and video memory 56 do not maintain stored contents when the computing device is turned off. Examples of volatile memories include random access memories (RAM), dynamic random access memories (DRAM), static random access memories (SRAM), and other forms of volatile memories known in the art. In some examples, storage device 54 is used to store program instructions for execution by processors 18.

Storage devices 54 and video memory 56, in some examples, also include one or more computer-readable storage media. Storage devices 54 and video memory 56 may be configured to store larger amounts of information than volatile memory. Storage devices 54 and video memory 56 may further be configured for long-term storage of information. In some examples, storage devices 54 and video memory 56 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Communication channels 48 may interconnect each of the components 18, 44, 46, 50, 16, 52, 54, 56, 58, and 60 for inter-component communications (physically, communicatively, and/or operatively). In some examples, communication channels 48 may include a system bus, a network connection, an inter-process communication data structure, or any other method for communicating data.

One or more communication units 44 of central computing device 14 may communicate with external devices, such as a field computing device, via one or more wired and/or wireless networks by transmitting and/or receiving network signals on the one or more networks. Communication units 44 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, central computing device 14 utilizes communication units 44 to wirelessly communicate with another computing device that is operably coupled to central computing device 14, such as field computing device 4 of FIG. 1.

One or more processors 18, in one example, are configured to implement functionality and/or process instructions for execution within central computing device 14. For example, processors 18 may be capable of processing instructions stored in storage device 54. Examples of processors 18 may include, any one or more of a microprocessor, a controller, a digital signal processor (DSP), an application specific integrated circuit (ASIC), a field-programmable gate array (FPGA), or equivalent discrete or integrated logic circuitry.

In some examples, central computing device 14 may include one or more sensors 46. One or more of sensors 46 may measure one more measurands. Examples of one or more of sensors 46 may include one or more position sensors (e.g., a global positioning system (GPS) sensor, an indoor positioning sensor, or the like), one or more motion/orientation sensors (e.g., an accelerometer, a gyroscope), a light sensor, a temperature sensor, a pressure (or grip) sensor, a physical switch, a proximity sensor, and one or more biosensors that can measure properties of the skin/blood, such as alcohol, blood sugar, heart rate, and/or perspiration level.

In some examples, central computing device 14 may receive a field media stream from a field computing device (e.g., field computing device 4 of FIG. 1). The field media stream may include timing information. In such examples, central computing device 14 may include timing information in the second media stream such central computing device 14 may align the timing information of the second media stream to the timing information of the field media stream. The timing information may include a time corresponding to the time that the field media stream begins, such as the time of day or the 0:00:00 indication, and a time corresponding to the time that the field media stream ends, such as the time of day later than the first time of day or the time in the form of #:##:##, wherein the #'s indicate numbers describing the length of the field media stream. In some instances, the timing information may instead or additionally include frame numbers. However, central computing device 14 may still execute the techniques of FIG. 3 without having first received such a field media stream.

The techniques described herein may measure and compensate for network latency so that the video stream and overlay are synchronized. Tactical networks can experience significant network latency, due to the number of hops taken across an ad-hoc network to get from the field device to the expert device. This delay could cause the overlay video (hands) seen on the field device to not be time-synchronized with the original video stream from the field device. For example, if there is a one-second network latency between the field and expert device, so that it takes one second for the video stream to travel from the field device to the expert device and then an additional one second for the overlay stream to travel from the expert device to the field device, the result is that the overlay image will be two seconds delayed from the video from the field device's camera.

To solve this problem without increasing bandwidth usage, the techniques described herein may buffer a copy of the original video stream locally on the field device, synchronize the timestamps of the original and overlay video streams, and display the buffered original video stream on the field device on a delay that matches the measured delay of the overlay stream. The result is that the user of the field device will see a slightly-delayed video stream, relative to what the device's camera is recording, but the user is guaranteed that the overlay and video stream that he sees on his device are the same as what the medical expert sees on her device.

In accordance with techniques of this disclosure, image capture module 58 of central computing device 14 may first capture an image of a background environment (e.g., background environment 20 of FIG. 1), possibly utilizing camera 16. The background environment may be local to central computing device 14. For instance, the background environment may be any background environment, such as a solid-colored or patterned background "stage" or a general room containing various objects, among other things.

Image capture module 58 of central computing device 14 may then record a first media stream, possibly utilizing camera 16. The first media stream may include at least a portion of the image of the previously captured background environment and a representation of at least one movement of at least one object (e.g., image of the medical expert's hand, a vector representation of the medical expert's hand, etc.) through said background environment.

Image alteration module 60 of central computing device 14 may remove the image of background environment 20 from the first media stream to create a second media stream. The second media stream, accordingly, may only include the at least one movement of the object through the background environment without actually including the image of the background environment. By removing the image of the background environment, the second media stream will have a smaller size than the first media stream, allowing it to cross a low-bandwidth node network quicker and more efficiently. In some examples, image alteration module 60 may further replace the object in the second media stream with a digital image different than the object. For instance, image alteration module 60 may replace the object in the second media stream with a vector graphic, an arrow graphic, or a low-resolution representation of the object, such as a digital hand or pointer object.

The image of the background environment may be removed from the first media stream in any way suitable for the techniques described herein. For instance, if the background environment is a solid color, image alteration module 60 may detect a pixel color value present in the image of the background environment and remove any pixel from each frame of the first media stream that matches or approximately matches (e.g., taking into account shading) the detected pixel color value of the pixels in the image of the background environment. If the background environment is a patterned background or a general room, the color-removal process may be repeated for each color found in the image of the background environment. In other examples, image alteration module 60 of central computing device 14 may compute a depth at which the background environment lies in the image of the background environment. Image alteration module 60 of central computing device 14 may then remove all objects from the first media stream found at that depth, leaving only the newly introduced object in the second media stream. These are merely examples of how the background environment may be removed from the first media stream. Any other technique available that results in the removal of the background environment from the first media stream may be utilized in accordance with the techniques of the current disclosure.

For instance, in another example of removing the image of background environment 20 from the second media stream, image alteration module 60 may store a set of one or more object patterns. Each object pattern in the set of one or more object patterns may be one of a possible shape or a possible color of a possible configuration of the at least one object. Image alteration module 60 may determine one or more portions of the first media stream that match an object pattern of the set of one or more object patterns. For each frame of the at least one frame of the first media stream, image alteration module 60 may remove each pixel of the first media stream that is outside of the one or more portions that match the object pattern. For example, image alteration module 60 may store different possible shapes and colors of hands. Image alteration module 60 may attempt to find a portion of the second media stream that matches one of the object patterns containing possible shapes and colors of hands. Determining that the found portion is a hand, image alteration module 60 may remove the pixels in the second media stream that are outside of the found portion, leaving only the hand in the second media stream.

In another example of removing the image of background environment 20 from the second media stream, image alteration module 60 may, for each frame of at least one frame of the second media stream, compare the respective frame of the first media stream to the image of the background environment. Image alteration module 60 may then remove each pixel of the second media stream with a color value equal to a color value of a corresponding pixel value in the image of the background environment. For instance, if camera 16 is in a fixed position, the background environment will not change between the image of the background environment and the filming of the second media stream. As such, if object 22 is in the middle of the second media stream, the pixel in the top-left corner of the second media stream may have a color value equal to the pixel in the top-left corner of the image of the background environment. As such, this pixel may be removed. Removing each matching pixel from each frame of the second media stream may leave only object 22 in the second media stream.

Central computing device 14, operating in a generally low-bandwidth environment, may perform further operations to reduce the bandwidth needed to efficiently send the second media stream to the field computing device. While the environment of the network is generally a low-bandwidth environment, if the available bandwidth on the network falls below a certain level, central computing device 14 may perform additional operations to ensure that central computing device 14 transmits the second media stream in an efficient manner. For instance, image alteration module 60 may determine a current bandwidth level of a network over which the second media stream will be transmitted. Image alteration module 60 may then compare the current bandwidth level to a bandwidth threshold associated with the second media stream. In some instances, the bandwidth threshold may be a static value for the particular network or a particular environment that the network is situated in, either set by an administrator or automatically set based on various network characteristics of the network. In other instances, the bandwidth threshold may be dynamically set based on characteristics of the second media stream, central computing device 14, or field computing device 4. For instance, certain devices may require a certain minimum bandwidth in order to operate effectively. As another example, central computing device 14 may set the bandwidth threshold based on the size of the second media stream (e.g., such that, given the size of the second media stream, central computing device 14 is able to fully send the second media stream within a particular amount of time). For instance, if the second media stream is 6600 Kilobytes (KB) in size, and the system is set to fully transmit the second media stream within one minute, central computing device 14 may set the bandwidth threshold to equal 110 KB/sec. In still other examples, such as in a live streaming situation, the bandwidth threshold may be set such that field computing device 4 is able to receive and play the second media stream at at least a minimum quality level (e.g., without skipping or buffering, or at a particular frames per second rate).

To detect available network bandwidth, bandwidth-sensing algorithms may be implemented. A first algorithm uses Variable Packet Size Probing (VPSP). VPSP transmits a series of packets of known size and measures how long it takes to send each packet and receive a reply. This method is useful for measuring bandwidth on low-jitter networks (networks with consistent node-to-node transmit times). A second algorithm sends out a specified number of maximum-size UDP packets. The receiver records the time that the packets are received. This method is useful for measuring bandwidth on high-jitter networks.

Central computing device 14 may then automatically choose and later adjust video stream parameters (e.g., quality) based on detected bandwidth. These techniques also support user adjustment of video stream parameters. The automated bandwidth-adjustment system enables warfighters and medical personnel, for example, to obtain a high-quality video stream with minimal training or configuration, producing a user-friendly experience. The manual parameter adjustment capability gives users the ability to alter the video stream settings to handle unusual situations. For example, in one particular scenario, a medical expert may require a higher-resolution image but does not require a high video frame rate. In this case, the expert could quickly adjust the settings to increase the image resolution, which would automatically lower the frame rate to fit within available network bandwidth.

As part of this task, the techniques described herein utilize automated algorithms and manual guidelines for using and switching between different video parameters. For manual controls, these guidelines may come in the form of documentation and in-app suggestions for altering the video stream. For example, a medical expert could manually request a higher-resolution stream for a particular situation and decide whether to lower the bandwidth by converting the stream to greyscale or by lowering the framerate. Automated parameter selection algorithms will be used by central computing device 14 to determine initial video stream parameters, such as resolution and frame rate, based on the initial network bandwidth measurements. During the streaming session, central computing device 14 may periodically reassess the network bandwidth and streaming performance and automatically make parameter adjustments as necessary. This enables a video stream to immediately start with the maximum video quality regardless of the available network bandwidth and to quickly adapt to changing network conditions.

Responsive to determining that the current bandwidth level of the network is less than the bandwidth threshold, central computing device 14 may alter the second media stream to reduce an amount of data transmitted in the second media stream. In reducing the amount of data transmitted, central computing device 14 may do so to an extent that central computing device 14 may effectively and efficiently transmit the second media stream according to the parameters of the network (e.g., within a particular time limit given the available bandwidth, etc.).

In some instances, image alteration module 60 may alter the second media stream by applying one or more real-time video filters to the second media stream, where the one or more real-time video filters each result in reducing the size of the second media stream. Image alteration module 60 may select the one or more real-time video filters from a plurality of video filters based on the comparison of the current bandwidth level to the bandwidth threshold (e.g., how much the size must be reduced to satisfy the bandwidth requirements of the system, the stream, and the network).

In other instances, image alteration module 60 may alter the second media stream by converting the media stream to an image. Image alteration module 60 may do so by selecting a single frame from the second media stream as a static image representative of the second media stream and replacing the second media stream with the static image. In transmitting the second media stream, image alteration module 60 may transmit the static image to the field computing device via the network. This may address the case where bandwidth levels are extremely low and transmitting a larger video would result in great inefficiencies in the network.

With the addition of sending static images, a new option for compression is available. By varying the compression within the image, central computing device 14 may further decrease its network footprint. With this feature, a medic would take a picture and then highlight the most important area(s) of the image. The techniques described herein may then use more-aggressive compression on the area(s) that were not selected and higher-quality compression on the highlighted area(s). This would allow the same image to traverse the network faster and with less bandwidth usage. Additionally, machine learning could be applied to this process, enabling central computing device 14 to automatically select the important areas, creating a seamless improvement to the annotation process. Once the machine learning engine is sufficiently advanced, it may also be possible to also apply this functionality to streaming video. This machine learning implementation would further decrease the bandwidth used by the video.

In other instances, such as when the network is a bonded network, or a network that includes a plurality of radios in contact with one another to expand the reach of the network, image alteration module 60 may perform a segmenting operation on the second media stream. For example, image alteration module 60 may segment the second media stream into a plurality of media stream segments, where each media stream segment has a respective size small enough to be transmitted efficiently given the constraints of the network. Image alteration module 60 may then utilize different radios of the bonded network by transmitting each media stream segment to a different one of the plurality of radios of the bonded network, as the bandwidth restrictions would be determined for each individual radio communication rather than on the network as a whole. Image alteration module 60 may include reassembly indications in each media stream segment such that field computing device 4 may reliably reassemble the various media stream segments upon receipt, such as ordering information. By segmenting the second media stream, image alteration module 60 may take advantage of the multiple available connections, as opposed to traditional connections where the entire file must be sent over the same connection.

Bonded connections/networks work by using multiple uplinks to achieve the needed bandwidth. In this case, one end-user device (EUD) (e.g., central computing device 14) would be connected to multiple radios. Each radio transmits part of the video steam, and the receiver's device reassembles the video stream properly. This could be accomplished in a few ways: by an application itself, by an operating system, or by a device bridging the receiver's device and the bonded radios. Each of these approaches may different trade-offs. The bridge device introduces a new piece of hardware but enables other network devices to take advantage of the bonded connection, as any device needing a network connection can attach to the bridge and use the higher-bandwidth bonded connection. Implementing bonding at the operating system level enables this feature for any software on the receiver, without involving additional hardware, but this feature would need to be implemented on each potential receiver operating system. Finally, implementing bonding in the application software addresses the issue without additional hardware or operating system modifications, but involves manually altering video-streaming libraries (rather than taking advantage of existing, standard networking capabilities), and the benefit may only apply to the application software itself and not other software on the receiver.

In still other instances, image alteration module 60 may alter the second media stream by compressing the second media stream using one or more compression techniques based on an amount that the current bandwidth level is less than the bandwidth threshold. Image alteration module 60 may select the one or more compression techniques from a plurality of compression techniques using, e.g., a machine learning model. Various compression techniques may have different levels of effectiveness in reducing the size of a file, particularly with different types of files. As such, after transmitting the second media stream, image alteration module 60 may determine a time to completion for transmitting the second media stream and update the machine learning model based on the time to completion and a threshold time to completion associated with the network. For example, if image alteration module 60 selects a particular compression technique, central computing device 14 may have limited data as to how effective the technique is. After completing the compression and the transmitting, image alteration module 60 may update the machine learning model to include the time to completion for the transmission, including as the time to completion compares to any threshold time to completion desired for the network. Image alteration module 60 may use this data in the machine learning model during future selection processes for compression.

Machine learning techniques may include any techniques that enable image alteration module 60 to update the machine learning model to more accurately and more efficiently select and apply compression techniques to media streams described herein. For instance, image alteration module 60 may utilize one or more of decision tree learning, association rule learning, artificial neural networks, deep learning, inductive logic programming, support vector machines, clustering, Bayesian networks, reinforcement learning, representation learning, similarity and metric learning, sparse dictionary learning, and/or rule-based machine learning in implementing machine learning techniques and the machine learning model. Image alteration module 60 may utilize machine learning techniques to analyze media streams and select the most effective and efficient compression technique for the particular media stream.

One example machine learning model that image alteration module 60 may leverage includes a neural network system. Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

A neural network system may receive multiple input feature values and process the input feature values to generate one or more network outputs. Each input feature value may describe a particular feature of an input data item, and each network output may describe a computed property of the input data item. For example, an input feature value may describe a media stream size/resolution, a media stream file type, a media stream length, the presence of audio in the stream, etc. Each input feature value belongs to an input feature value type and has a raw value. An input feature value type indicates the feature of the input data item that the corresponding input feature value describes. The raw value in an input feature value is a value assigned to the input feature value type.

The neural network system may include a discretization layer, a sparse calibration layer, and one or more additional layers. The discretization layer determines a total range of values for each input feature value type and discretizes these features prior to being fed into the main deep neural network. A total range of values for an input feature value type includes a minimum value and a maximum value for the input feature value type. The discretization layer can determine a minimum and a maximum value of input feature values belonging to an input feature value type in a collection of input training data as the minimum value and the maximum value for the input feature value type respectively. The discretization layer can also use a predetermined minimum value and maximum value for the input feature values belonging to a particular input feature value type as the minimum value and the maximum value for the particular input feature value type respectively. The discretization layer divides, for each input feature value type, the total range of values for the input feature value type into multiple bins, e.g., multiple bins that each include an equal range of possible values. Each bin includes a range of possible values in the total range of values for the input feature value type.

By converting an input feature value to multiple discretized feature values that each has a significant variance in value, the neural network system can increase the significance of the feature values used by the additional layers to make inferences and generate multiple useful pieces of information from the input feature value. By doing this, the neural network system can increase the accuracy of inferences made by the additional layers. This technique is especially useful for processing collections of input feature values that are generally sparse, e.g., generally include mostly zero or low values.

A sparse calibration layer of the neural network system obtains the discretized feature values and generates refined feature values by normalizing the discretized feature values to generate normalized feature values and applying a type-specific bias value to each normalized feature value. This layer has two main extras compared to other sparse layers out there, namely a normalization scheme that prevents gradients from exploding, and a per-feature bias to distinguish between the absence of a feature and the presence of a zero-valued feature. The sparse calibration layer can normalize a discretized feature value by dividing a value associated with a discretized value type of the discretized feature value by a maximum value for the input feature value type that corresponds to an input feature value using which the discretized feature value is generated. The sparse calibration layer also applies, e.g., adds, a type-specific bias value to each normalized feature value. A type-specific bias value is associated with a particular input feature value type and is common to all normalized feature values that are generated using input feature values belonging to the particular input feature value type.

Another layer of the neural network system may include a sampling scheme layer associated with a calibration layer. Stacked neural networks usually explore the space of solutions much better when the training dataset contains a similar number of positive and negative examples. However, hand-tuning a training dataset in this manner may lead to uncalibrated output predictions. Thus, a custom isotonic calibration layer may recalibrate and output actual probabilities.

The additional layers of the neural network system may include one or more other neural network layers, such as one or more feedforward fully-connected layers, one or more feedforward convolutional layers, one or more recurrent layers, one or more testing layers, one or more softmax layers, one or more calibration layers, and the likes. The additional layers process the refined feature values to generate the network outputs.

A training engine can train the sparse calibration layer and the additional layers using any neural network training algorithm, such as a training algorithm that relies on back-propagation with gradient descent. The training engine can use observed data, such as observed data about the effectiveness and efficiency of various compression techniques, as the target output data for training.

Deep learning models, such as the stacked neural network system described above, are models that are intrinsically modular. Deep learning modules may be composed in various ways (stacked, concatenated, etc.) to form a computational graph. The parameters of this graph may then be learned, such as by using back-propagation and stochastic gradient descent on mini-batches.

Low-level modules used by deep learning models that may be any hardware or software module configured to compute the output from input and necessary gradients. Some such modules may perform basic operations on chunks of data, potentially letting the user specify the algorithm in its preferred tensor manipulation package, and trusting the library to generate the computational graph itself. In other examples, the computational graph may be dynamic and change from one mini-batch to the other. Deep learning techniques may also be scalable, as these models learn from mini-batches of data, the total dataset size can be arbitrarily large.

In other instances, in altering the second media stream, image alteration module 60 may convert the second media stream to greyscale (e.g., removing the color from the second media stream and replacing the color with a spectrum of white/black/grey shades). This reduces the size of the second media stream even further.

In some instances, the second media stream may include both a video stream and an audio stream. As such, responsive to determining that the current bandwidth level of the network is less than the bandwidth threshold, image alteration module 60 may alter each of the video stream and the audio stream to reduce the amount of data transmitted in the second media stream when transmitted over the network. In some instances, in altering the audio stream, image alteration module 60 may select an audio compression technique from a plurality of audio compression techniques based on the current bandwidth level and the bandwidth threshold, and then apply the audio compression technique to the audio stream. In other instances, in addition to or in place of the compression techniques, image alteration module 60 may remove background noise from the audio stream, leaving only the foreground sound (e.g., the vocal instructions from the medical expert) and decreasing the overall file size.

In this task, the techniques described herein may automatically modify the streaming audio parameters in response to available bandwidth. This includes changing the audio compression based on the bandwidth. These techniques also includes turning off audio transmission when the user is not speaking and using background noise removal to improve the compressibility of the audio stream. These features will decrease the bandwidth usage even further while improving its usability.

Central computing device 14 may then transmit the second media stream to the field computing device via the network. In instances where image capture module 58 utilizes a microphone of camera 16 to capture audio data, the second media stream may further include the audio stream containing the captured audio data.

Field computing device 4 may use the second media stream and the field media stream to assemble an enhanced message stream by aligning timing information of the second media stream and the field media stream. For instance, in aligning the timing information, central computing device 14 may determine, based at least in part on the timing information of the field media stream, a starting time of the field media stream and an ending time of the field media stream. Central computing device 14 may then determine a starting time for the second media stream and an ending time for the second media stream. The starting time for the second media stream may be between the starting time of the field media stream and the ending time of the field media stream. Further, the ending time for the second media stream may be after the starting time of the second media stream and before the ending time of the field media stream. As such, the timing information of the second media stream would be within the timing information of the field media stream and using the same time units as the field media stream.

In some examples, central computing device 14 may further alter the aspect ratio of the second media stream. For instance, image alteration module 60 may resize the second media stream such that the aspect ratio of the second media stream matches an aspect ratio of the field media stream.

In one use case of the above techniques, a medical expert at a remote location may receive a field media stream from a field media device showing an injury, such as a gashed leg. After analyzing the injury to the leg, the medical expert may determine that a portion of the gashed leg may need to be moved or set in a specific manner, or that medical treatment must be provided to a specific portion of the gashed leg. Image capture module 58 of central computing device 14 may capture an image of a background environment that the medical expert will use as the background for the instructional video the medical expert is about to record. Image capture module 58 of central computing device 14 may then record a first media stream of the medical expert moving his/her hands through the background environment, showing how the gashed leg must be sutured. Image alteration module 60 may then remove the image of the background environment from the first media stream to obtain a second media stream that only includes the medical expert's hands moving through space without the image of the background environment. By removing the background environment, the file size will be much smaller than a media stream with the background environment. The smaller file size allows for faster and more efficient transfer of the media stream to the field computing device across a low-bandwidth node network.

After creating the second message stream of just the medical expert's hands moving through space, image alteration module 60 may determine the new file size is 1000 KB, and the current bandwidth on the network is 30 KB/sec. However, the file must be sent within 20 seconds, meaning that the maximum file size allowable is 600 KB. As such, image alteration module 60 may further alter the second media stream using any of the techniques described above in order to further reduce the file size of the second media stream.

In other examples, where the media stream is meant to be livestreamed, central computing device 14 may determine an amount that the second media stream must be compressed such that the second media stream may be transmitted to the field computing device without buffering or skipping, or such that the second media stream has a minimum frames per second watchability on the field computing device.

Figure 4:
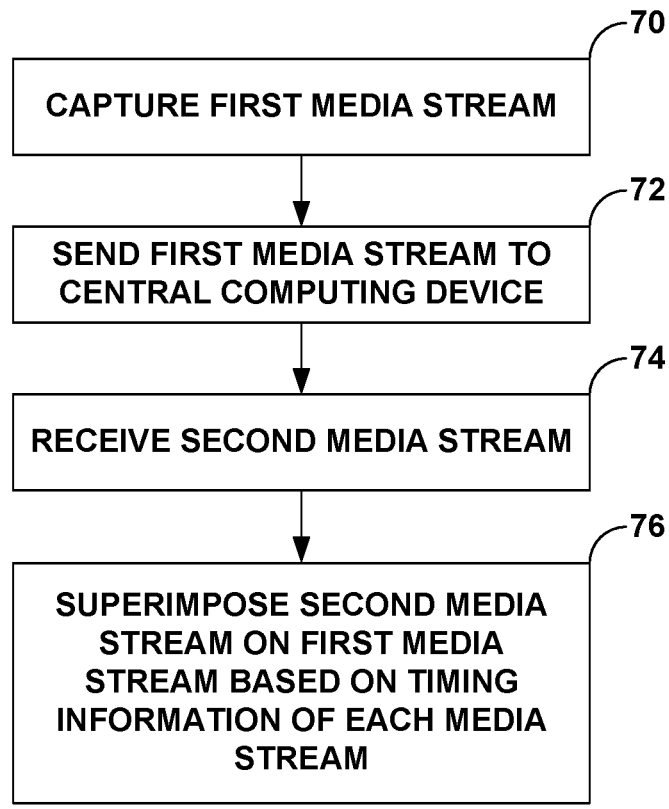
FIG. 4 is a flow diagram illustrating example operations of a field computing device that implements location techniques in accordance with one or more aspects of this disclosure.

FIG. 4 is a flow diagram illustrating example operations of a field computing device that implements location techniques in accordance with one or more aspects of this disclosure. The techniques of FIG. 4 may be performed by one or more processors of a computing device, such as field computing device 4 illustrated in FIG. 1 and/or FIG. 2. For purposes of illustration only, the techniques of FIG. 4 are described within the context of field computing device 4 of FIG. 1, although computing devices having configurations different than that of field computing device 4 may perform the techniques of FIG. 4.

In accordance with techniques of the current disclosure, field computing device 4 may capture (70) a first media stream. The first media stream includes timing information. The timing information may include a time that the media stream begins, such as a time of day or a 0:00:00 indication, and a time that the media stream ends, such as a time of day later than the first time of day or a time in the form of #:##:##, wherein the #'s indicate numbers describing the length of the first media stream. The first media stream may include a representation of an object, which may, in certain non-limiting examples, be a body part containing an injury or an ailment that is to be treated medically. Field computing device 4 may send (72) the first media stream to a central computing device (e.g., central computing device 14 of FIG. 1) across a node network (e.g., node network 12 of FIG. 1).

Field computing device 4 may receive (74), from the central computing device, a second media stream. The second media stream may include at least one movement of a second object without any images of a background environment. The second media stream may further include timing information corresponding to the timing information of the first media stream.

Field computing device 4, with the received second media stream and the originally captured first media stream, may superimpose (76) the received second media stream on the first media stream. Field computing device 4 may perform the superimposing based at least in part on aligning the timing information of the second media stream with the timing information of the first media stream. For instance, field computing device 4 may determine, based at least in part on the timing information of the second media stream, a starting time for the second media stream and an ending time for the second media stream. Field computing device 4 may then display the first media stream. Field computing device 4 may display the second media stream on top of the first media stream and simultaneously with the first media stream when the first media stream reaches a frame with timing information equal to the starting time of the second media stream, whether it is a frame number or a time. Field computing device 4 may then remove the second media stream from display when the first media stream reaches a frame with timing information equal to the ending time of the second media stream. In some examples, when the second media stream contains audio, field computing device 4 may further replace any audio in the first media stream with the audio of the second media stream.

In some examples, field computing device 4 may alter the size of the received second media stream. For instance, field computing device 4 may resize the received second media stream such that it is in the same aspect ratio as the recorded first media stream.

The superimposed video provides the field computing device with a treatment for the injury. For instance, where the first object is a gashed leg, the second object would be overlaid on top of the gashed leg, and would appear to move along the gashed leg in a way necessary for treatment of the gashed leg to occur, such as a movement to suture the wound. By performing the superimposing locally on field computing device 4 rather than field computing device 4 receiving a full media stream of the treatment over a low-bandwidth node network, field computing device 4 is able to receive a quality instructional treatment in a shorter time than if field computing device 4 waited for the entirety of a full media stream to be received.

Figure 5:
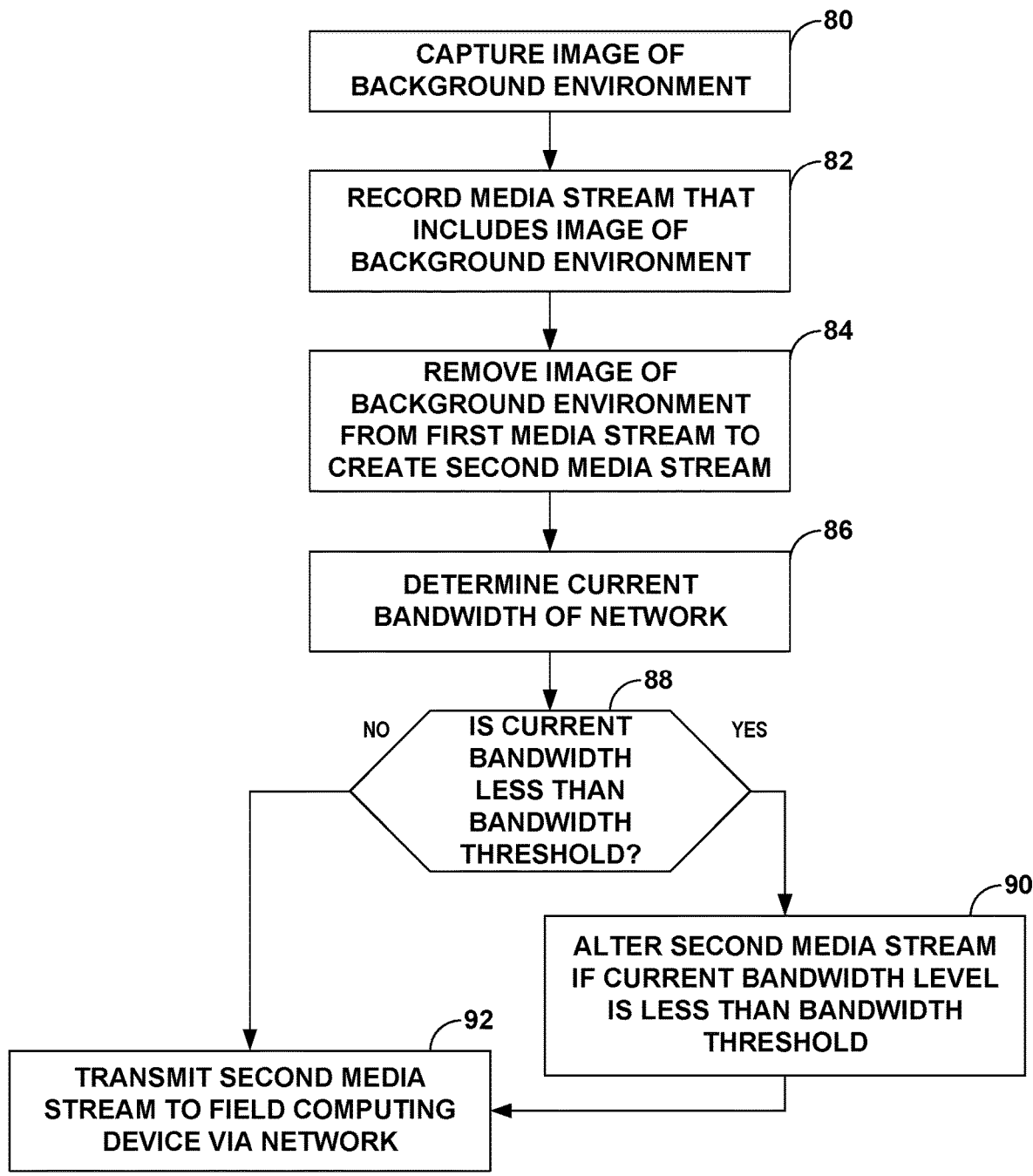
FIG. 5 is a flow diagram illustrating example operations of a central computing device that implements location techniques in accordance with one or more aspects of this disclosure.

FIG. 5 is a flow diagram illustrating example operations of a central computing device that implements location techniques in accordance with one or more aspects of this disclosure. The techniques of FIG. 5 may be performed by one or more processors of a computing device, such as central computing device 14 illustrated in FIG. 1 and/or FIG. 3. For purposes of illustration only, the techniques of FIG. 5 are described within the context of central computing device 14 of FIG. 1, although computing devices having configurations different than that of central computing device 14 may perform the techniques of FIG. 5.

While shown as a complete process in FIG. 5, various portions of FIG. 5 may be performed separately from other portions. For instance, central computing device 14 may perform the bandwidth determination portion of this process, and the operations resulting from the bandwidth determination, without necessarily performing the initial media stream capture and background removal operations.

In some examples, central computing device 14 may receive a field media stream from a field computing device (e.g., field computing device 4 of FIG. 1). The field media stream may include timing information. In such examples, central computing device 14 may include timing information in the second media stream such central computing device 14 may align the timing information of the second media stream to the timing information of the field media stream. The timing information may include a time corresponding to the time that the field media stream begins, such as the time of day or the 0:00:00 indication, and a time corresponding to the time that the field media stream ends, such as the time of day later than the first time of day or the time in the form of #:##:##, wherein the #'s indicate numbers describing the length of the field media stream. In some instances, the timing information may instead or additionally include frame numbers. However, central computing device 14 may still execute the techniques of FIG. 5 without having first received such a field media stream.

In accordance with techniques of this disclosure, central computing device 14 may capture (80) an image of a background environment (e.g., background environment 20 of FIG. 1), possibly utilizing camera 16. The background environment may be local to central computing device 14. For instance, the background environment may be any background environment, such as a solid-colored or patterned background "stage" or a general room containing various objects, among other things.

Central computing device 14 may then record (82) a first media stream, possibly utilizing camera 16. The first media stream may include at least a portion of the image of the previously captured background environment and a representation of at least one movement of at least one object (e.g., image of the medical expert's hand, a vector representation of the medical expert's hand, etc.) through said background environment.

Central computing device 14 may remove (84) the image of background environment 20 from the first media stream to create a second media stream. The second media stream, accordingly, may only include the at least one movement of the object through the background environment without actually including the image of the background environment. By removing the image of the background environment, the second media stream will have a smaller size than the first media stream, allowing it to cross a low-bandwidth node network quicker and more efficiently. In some examples, central computing device 14 may further replace the object in the second media stream with a digital image different than the object. For instance, central computing device 14 may replace the object in the second media stream with a vector graphic, an arrow graphic, or a low-resolution representation of the object, such as a digital hand or pointer object.

The image of the background environment may be removed from the first media stream in any way suitable for the techniques described herein. For instance, if the background environment is a solid color, central computing device 14 may detect a pixel color value present in the image of the background environment and remove any pixel from each frame of the first media stream that matches or approximately matches (e.g., taking into account shading) the detected pixel color value of the pixels in the image of the background environment. If the background environment is a patterned background or a general room, the color-removal process may be repeated for each color found in the image of the background environment. In other examples, central computing device 14 of central computing device 14 may compute a depth at which the background environment lies in the image of the background environment. Central computing device 14 may then remove all objects from the first media stream found at that depth, leaving only the newly introduced object in the second media stream. These are merely examples of how the background environment may be removed from the first media stream. Any other technique available that results in the removal of the background environment from the first media stream may be utilized in accordance with the techniques of the current disclosure.

For instance, in another example of removing the image of background environment 20 from the second media stream, central computing device 14 may store a set of one or more object patterns. Each object pattern in the set of one or more object patterns may be one of a possible shape or a possible color of a possible configuration of the at least one object. Central computing device 14 may determine one or more portions of the first media stream that match an object pattern of the set of one or more object patterns. For each frame of the at least one frame of the first media stream, central computing device 14 may remove each pixel of the first media stream that is outside of the one or more portions that match the object pattern. For example, central computing device 14 may store different possible shapes and colors of hands. Central computing device 14 may attempt to find a portion of the second media stream that matches one of the object patterns containing possible shapes and colors of hands. Determining that the found portion is a hand, central computing device 14 may remove the pixels in the second media stream that are outside of the found portion, leaving only the hand in the second media stream.

In another example of removing the image of background environment 20 from the second media stream, central computing device 14 may, for each frame of at least one frame of the second media stream, compare the respective frame of the first media stream to the image of the background environment. Central computing device 14 may then remove each pixel of the second media stream with a color value equal to a color value of a corresponding pixel value in the image of the background environment. For instance, if camera 16 is in a fixed position, the background environment will not change between the image of the background environment and the filming of the second media stream. As such, if object 22 is in the middle of the second media stream, the pixel in the top-left corner of the second media stream may have a color value equal to the pixel in the top-left corner of the image of the background environment. As such, this pixel may be removed. Removing each matching pixel from each frame of the second media stream may leave only object 22 in the second media stream.

Central computing device 14, operating in a generally low-bandwidth environment, may perform further operations to reduce the bandwidth needed to efficiently send the second media stream to the field computing device. While the environment of the network is generally a low-bandwidth environment, if the available bandwidth on the network falls below a certain level, central computing device 14 may perform additional operations to ensure that central computing device 14 transmits the second media stream in an efficient manner. For instance, central computing device 14 may determine (86) a current bandwidth level of a network over which the second media stream will be transmitted. Central computing device 14 may then compare (88) the current bandwidth level to a bandwidth threshold associated for the network. In some instances, the bandwidth threshold may be a static value for the particular network or a particular environment that the network is situated in, either set by an administrator or automatically set based on various network characteristics of the network. In other instances, the bandwidth threshold may be dynamically set based on characteristics of the second media stream, central computing device 14, or field computing device 4. For instance, certain devices may require a certain minimum bandwidth in order to operate effectively. As another example, central computing device 14 may set the bandwidth threshold based on the size of the second media stream (e.g., such that, given the size of the second media stream, central computing device 14 is able to fully send the second media stream within a particular amount of time). For instance, if the second media stream is 1200 Kilobytes in size, and the system is set to fully transmit the second media stream within 30 seconds, central computing device 14 may set the bandwidth threshold to equal 40 KB/sec. In still other examples, such as in a live streaming situation, the bandwidth threshold may be set such that field computing device 4 is able to receive and play the second media stream at at least a minimum quality level (e.g., without skipping or buffering, or at a particular frames per second rate).

Responsive to determining that the current bandwidth level of the network is less than the bandwidth threshold ("YES" branch of 88), central computing device 14 may alter (90) the second media stream to reduce an amount of data transmitted in the second media stream. In reducing the file size, central computing device 14 may do so to an extent that central computing device 14 may effectively and efficiently transmit the second media stream according to the parameters of the network (e.g., within a particular time limit given the available bandwidth, etc.).

In some instances, central computing device 14 may alter the second media stream by applying one or more real-time video filters to the second media stream, where the one or more real-time video filters each result in reducing the size of the second media stream. Central computing device 14 may select the one or more real-time video filters from a plurality of video filters based on the comparison of the current bandwidth level to the bandwidth threshold (e.g., how much the file size must be reduced to satisfy the bandwidth requirements of the system and the network).

In other instances, central computing device 14 may alter the second media stream by converting the media stream to an image. Central computing device 14 may do so by selecting a single frame from the second media stream as a static image representative of the second media stream and replacing the second media stream with the static image. In transmitting the second media stream, central computing device 14 may transmit the static image to the field computing device via the network. This may address the case where bandwidth levels are extremely low and transmitting a larger video would result in great inefficiencies in the network.

In other instances, such as when the network is a bonded network, or a network that includes a plurality of radios in contact with one another to expand the reach of the network, central computing device 14 may perform a segmenting operation on the second media stream. For example, central computing device 14 may segment the second media stream into a plurality of media stream segments, where each media stream segment has a respective size small enough to be transmitted efficiently given the constraints of the network. Central computing device 14 may then utilize different radios of the bonded network by transmitting each media stream segment to a different one of the plurality of radios of the bonded network, as the bandwidth restrictions would be determined for each individual radio communication rather than on the network as a whole. Central computing device 14 may include reassembly indications in each media stream segment such that field computing device 4 may reliably reassemble the various media stream segments upon receipt, such as ordering information. By segmenting the second media stream, central computing device 14 may take advantage of the multiple available connections, as opposed to traditional connections where the entire file must be sent over the same connection.

In still other instances, central computing device 14 may alter the second media stream by compressing the second media stream using one or more compression techniques based on an amount that the current bandwidth level is less than the bandwidth threshold. Central computing device 14 may select the one or more compression techniques from a plurality of compression techniques using a machine learning model. Various compression techniques may have different levels of effectiveness in reducing the size of a file, particularly with different types of files. As such, after transmitting the second media stream, central computing device 14 may determine a time to completion for transmitting the second media stream and update the machine learning model based on the time to completion and a threshold time to completion associated with the network. For example, if central computing device 14 selects a particular compression technique, central computing device 14 may have limited data as to how effective the technique is. After completing the compression and the transmitting, central computing device 14 may update the machine learning model to include the time to completion for the transmission, including as the time to completion compares to any threshold time to completion desired for the network. Central computing device 14 may use this data in the machine learning model during future selection processes for compression.

In other instances, in altering the second media stream, central computing device 14 may convert the second media stream to greyscale (e.g., removing the color from the second media stream and replacing the color with a spectrum of white/black/grey shades). This reduces the size of the second media stream even further.

In some instances, the second media stream may include both a video stream and an audio stream. As such, responsive to determining that the current bandwidth level of the network is less than the bandwidth threshold, central computing device 14 may alter each of the video stream and the audio stream to reduce the amount of data transmitted in the second media stream when transmitted over the network. In some instances, in altering the audio stream, central computing device 14 may select an audio compression technique from a plurality of audio compression techniques based on the current bandwidth level and the bandwidth threshold, and then apply the audio compression technique to the audio stream. In other instances, in addition to or in place of the compression techniques, central computing device 14 may remove background noise from the audio stream, leaving only the foreground sound (e.g., the vocal instructions from the medical expert) and decreasing the overall file size.

After altering the second media stream, or if the current bandwidth is not less than the bandwidth threshold ("NO" branch of 88), central computing device 14 may then transmit (92) the second media stream to the field computing device via the network. In instances where image capture module 58 utilizes a microphone of camera 16 to capture audio data, the second media stream may further include the audio stream containing the captured audio data.

Field computing device 4 may use the second media stream and the field media stream to assemble an enhanced message stream by aligning timing information of the second media stream and the field media stream. For instance, in aligning the timing information, central computing device 14 may determine, based at least in part on the timing information of the field media stream, a starting time of the field media stream and an ending time of the field media stream. Central computing device 14 may then determine a starting time for the second media stream and an ending time for the second media stream. The starting time for the second media stream may be between the starting time of the field media stream and the ending time of the field media stream. Further, the ending time for the second media stream may be after the starting time of the second media stream and before the ending time of the field media stream. As such, the timing information of the second media stream would be within the timing information of the field media stream and using the same time units as the field media stream.

In some examples, central computing device 14 may further alter the aspect ratio of the second media stream. For instance, image alteration module 60 may resize the second media stream such that the aspect ratio of the second media stream matches an aspect ratio of the field media stream.

By way of example, and not limitation, such computer-readable storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium may include a non-transitory medium. The term "non-transitory" indicates that the storage medium is not embodied in a carrier wave or a propagated signal. In certain examples, a non-transitory storage medium may store data that can, over time, change (e.g., in RAM or cache).

Various examples of the disclosure have been described. Any combination of the described systems, operations, or functions is contemplated. These and other examples are within the scope of the following claims.

The invention claimed is:

1. A method comprising:
removing, by one or more processors of a central computing device, an image of a background environment from a first media stream to create a second media stream, wherein the second media stream includes a representation of at least one movement of at least one object without the image of the background environment;
comparing, by the one or more processors of the central computing device, a current bandwidth level of a network to a bandwidth threshold, wherein the bandwidth threshold is associated with one or more of the second media stream, the central computing device, or a field computing device; and
responsive to determining that the current bandwidth level of the network is less than the bandwidth threshold:
selecting, by the one or more processors of the central computing device using a machine learning model, one or more compression techniques;
compressing, by the one or more processors of the central computing device, the second media stream using the one or more compression techniques;

transmitting, by the one or more processors of the central computing device and to the field computing device via the network, the second media stream;

after transmitting the second media stream, determining, by the one or more processors of the central computing device, a time to completion for transmitting the second media stream; and updating, by the one or more processors of the central computing device and based at least on the time to completion, the machine learning model.

2. The method of claim 1, wherein compressing the second media stream comprises compressing, by the one or more processors of the central computing device and based on an amount that the current bandwidth level is less than the bandwidth threshold, the second media stream using the one or more compression techniques.

3. The method of claim 1, wherein updating the machine learning model comprises updating, by the one or more processors of the central computing device, the machine learning model based on the time to completion and also on a threshold time to completion associated with the network.

4. The method of claim 1, wherein compressing the second media stream using the one or more compression techniques comprises applying, by the one or more processors of the central computing device, one or more real-time video filters to the second media stream.

5. The method of claim 4, further comprising:
selecting, by the one or more processors of the central computing device and based on the comparing of the current bandwidth level to the bandwidth threshold, the one or more real-time video filters from a plurality of video filters.

6. The method of claim 1, wherein compressing the second media stream using the one or more compression techniques comprises:
selecting, by the one or more processors of the central computing device, a single frame from the second media stream as a static image representative of the second media stream; and
replacing, by the one or more processors of the central computing device, the second media stream with the static image,
wherein transmitting the second media stream comprises transmitting, by the central computing device and to the field computing device via the network, the static image.

7. The method of claim 1,
wherein the network comprises a bonded network having a plurality of radios.

8. The method of claim 1,
wherein the second media stream comprises a video stream and an audio stream, and wherein compressing the second media stream using the one or more compression techniques comprises:
compressing, by the one or more processors of the central computing device, the video stream using a first compression technique; and
compressing, by the central computing device, the audio stream using a second compression technique, the second compression technique comprising an audio compression technique.

9. The method of claim 8, wherein compressing the audio stream comprises:
selecting, by the one or more processors of the central computing device and based on the current bandwidth level and the bandwidth threshold, the audio compression technique from a plurality of audio compression techniques; and
applying, by the one or more processors of the central computing device, the audio compression technique to the audio stream.

10. The method of claim 8, wherein compressing the audio stream comprises:
removing, by the one or more processors of the central computing device, background noise from the audio stream.

11. The method of claim 1, wherein compressing the second media stream using the one or more compression techniques comprises:
compressing, by the one or more processors of the central computing device and using a first compression technique, a first portion of the second media stream; and
compressing, by the one or more processors of the central computing device and using a second compression technique, a second portion of the second media stream, wherein the second compression technique is different than the first compression technique.

12. A central computing device comprising:
at least one processor; and
a storage device configured to store instructions that are executable by the at least one processor to:
remove an image of a background environment from a first media stream to create a second media stream, wherein the second media stream includes a representation of at least one movement of at least one object without the image of the background environment;
compare a current bandwidth level of a network to a bandwidth threshold, wherein the bandwidth threshold is associated with one or more of the second media stream, the central computing device, or a field computing device; and
responsive to determining that the current bandwidth level of the network is less than the bandwidth threshold:
select, using a machine learning model, one or more compression techniques;
compress the second media stream using the one or more compression techniques;
transmit, to the field computing device via the network, the second media stream;
after transmitting the second media stream, determine a time to completion for transmitting the second media stream; and
update, based at least on the time to completion, the machine learning model.

13. The central computing device of claim 12, wherein the instructions stored on the storage device that are executable by the at least one processor to compress the second media stream are further executable by the at least one processor to compress, based on an amount that the current bandwidth level is less than the bandwidth threshold, the second media stream using the one or more compression techniques.

14. The central computing device of claim 12, wherein the instructions stored on the storage device that are executable by the at least one processor to update the machine learning model are further executable by the at least one processor to update the machine learning model based on the time to completion and also on a threshold time to completion associated with the network.

15. The central computing device of claim 12, wherein the instructions stored on the storage device that are executable by the at least one processor to compress the second media stream using the one or more compression techniques are further executable by the at least one processor to apply one or more real-time video filters to the second media stream.

16. The central computing device of claim 12, wherein the instructions stored on the storage device that are executable by the at least one processor to compress the second media stream using the one or more compression techniques are further executable by the at least one processor to:
   select a single frame from the second media stream as a static image representative of the second media stream; and
   replace the second media stream with the static image, wherein the instructions stored on the storage device that are executable by the at least one processor to transmit the second media stream are further executable by the at least one processor to transmit, to the field computing device via the network, the static image.

17. The central computing device of claim 12,
   wherein the second media stream comprises a video stream and an audio stream, and wherein the instructions stored on the storage device that are executable by the at least one processor to compress the second media stream using the one or more compression techniques are further executable by the at least one processor to:
      compress the video stream using a first compression technique; and
      compress the audio stream using a second compression technique, the second compression technique comprising an audio compression technique.

18. The central computing device of claim 17, wherein the instructions stored on the storage device that are executable by the at least one processor to compress the audio stream are further executable by the at least one processor to: select, based on the current bandwidth level and the bandwidth threshold, the audio compression technique from a plurality of audio compression techniques; and apply the audio compression technique to the audio stream.

19. The central computing device of claim 12, wherein the instructions stored on the storage device that are executable by the at least one processor to compress the second media stream using the one or more compression techniques are further executable by the at least one processor to:
   compress, using a first compression technique, a first portion of the second media stream; and
   compress, using a second compression technique, a second portion of the second media stream, wherein the second compression technique is different than the first compression technique.

20. A non-transitory computer-readable storage medium storing instructions that, when executed, cause one or more processors of a central computing device to:
   remove an image of a background environment from a first media stream to create a second media stream, wherein the second media stream includes a representation of at least one movement of at least one object without the image of the background environment;
   compare a current bandwidth level of a network to a bandwidth threshold, wherein the bandwidth threshold is associated with one or more of the second media stream, the central computing device, or a field computing device; and
   responsive to determining that the current bandwidth level of the network is less than the bandwidth threshold:
      select, using a machine learning model, one or more compression techniques;
      compress the second media stream using the one or more compression techniques;
      transmit, to the field computing device via the network, the second media stream;
      after transmitting the second media stream, determine a time to completion for transmitting the second media stream; and
      update, based at least on the time to completion, the machine learning model.

\* \* \* \* \*